(12) United States Patent
Dubson et al.

(10) Patent No.: US 7,112,293 B2
(45) Date of Patent: Sep. 26, 2006

(54) METHOD AND APPARATUS FOR MANUFACTURING POLYMER FIBER SHELLS VIA ELECTROSPINNING

(75) Inventors: Alexander Dubson, Hadera (IL); Eli Bar, Hof Ha Carmel (IL)

(73) Assignee: Nicast Ltd., Lod (IL)

( * ) Notice: Subject to any disclaimer, the term of this patent is extended or adjusted under 35 U.S.C. 154(b) by 398 days.

(21) Appl. No.: 10/433,621

(22) PCT Filed: Dec. 17, 2001

(86) PCT No.: PCT/IL01/01168

§ 371 (c)(1),
(2), (4) Date: Jun. 18, 2003

(87) PCT Pub. No.: WO02/49678

PCT Pub. Date: Jun. 27, 2002

(65) Prior Publication Data

US 2004/0053553 A1 Mar. 18, 2004

Related U.S. Application Data

(60) Provisional application No. 60/276,956, filed on Mar. 20, 2001, provisional application No. 60/256,323, filed on Dec. 19, 2000.

(51) Int. Cl.
*B29C 41/02* (2006.01)

(52) U.S. Cl. ............... 264/10; 264/439; 425/174.8
(58) Field of Classification Search ..... 264/437–441.6, 264/10, 413, 465; 425/174.8
See application file for complete search history.

(56) References Cited

U.S. PATENT DOCUMENTS

| 2,491,889 | A | | 12/1949 | Bennett et al. |
| 3,280,229 | A | | 10/1966 | Simons |
| 3,425,418 | A | | 2/1969 | Chvapil et al. |
| 3,625,745 | A | | 12/1971 | Wright et al. |
| 3,688,317 | A | | 9/1972 | Kurtz |
| 3,860,369 | A | * | 1/1975 | Brethauer et al. ............. 425/3 |
| 4,044,404 | A | | 8/1977 | Martin et al. |
| 4,223,101 | A | | 9/1980 | Fine et al. |
| 4,323,525 | A | | 4/1982 | Bornat |
| 4,345,414 | A | | 8/1982 | Bornat |

(Continued)

FOREIGN PATENT DOCUMENTS

EP 0223374 5/1987

(Continued)

*Primary Examiner*—Mary Lynn Theisen

(57) ABSTRACT

An apparatus for manufacturing a polymer fiber shell from liquefied polymer is provided. The apparatus includes: (a) a precipitation electrode being for generating the polymer fiber shell thereupon; (b) a dispenser, being at a first potential relative to the precipitation electrode so as to generate an electric field between the precipitation electrode and the dispenser, the dispenser being for: (i) charging the liquefied polymer thereby providing a charged liquefied polymer; and (ii) dispensing the charged liquefied polymer in a direction of the precipitation electrode; and (c) a subsidiary electrode being at a second potential relative to the precipitation electrode, the subsidiary electrode being for modifying the electric field between the precipitation electrode and the dispenser.

28 Claims, 5 Drawing Sheets

U.S. PATENT DOCUMENTS

| | | | |
|---|---|---|---|
| 4,368,277 A | | 1/1983 | Burinsky et al. |
| 4,524,036 A | * | 6/1985 | Gilding et al. ............... 264/10 |
| 4,657,793 A | | 4/1987 | Fisher |
| 4,689,186 A | * | 8/1987 | Bornat ........................ 264/6 |
| 4,738,740 A | * | 4/1988 | Pinchuk et al. ............ 156/167 |
| 4,739,013 A | | 4/1988 | Pinchuk |
| 4,743,252 A | | 5/1988 | Martin et al. |
| 4,759,757 A | | 7/1988 | Pinchuk |
| 4,769,030 A | | 9/1988 | Pinchuk |
| 4,798,606 A | | 1/1989 | Pinchuk |
| 4,842,505 A | | 6/1989 | Annis et al. |
| 4,872,455 A | | 10/1989 | Pinchuk et al. |
| 4,880,002 A | | 11/1989 | MacGregor |
| 4,904,174 A | | 2/1990 | Moosmayer et al. |
| 4,905,367 A | | 3/1990 | Pinchuk et al. |
| 4,965,110 A | | 10/1990 | Berry |
| 4,990,158 A | | 2/1991 | Kaplan et al. |
| 4,997,600 A | | 3/1991 | Okumura et al. |
| 5,019,090 A | | 5/1991 | Pinchuk |
| 5,024,671 A | | 6/1991 | Tu et al. |
| 5,024,789 A | * | 6/1991 | Berry ........................ 264/6 |
| 5,084,085 A | | 1/1992 | Weldon et al. |
| 5,092,877 A | | 3/1992 | Pinchuk |
| 5,116,360 A | | 5/1992 | Pinchuk et al. |
| 5,133,742 A | | 7/1992 | Pinchuk |
| 5,147,725 A | | 9/1992 | Pinchuk |
| 5,226,913 A | | 7/1993 | Pinchuk |
| 5,298,255 A | | 3/1994 | Sawamoto et al. |
| 5,334,201 A | | 8/1994 | Cowan |
| 5,360,397 A | | 11/1994 | Pinchuk |
| 5,376,117 A | | 12/1994 | Pinchuk et al. |
| 5,383,928 A | | 1/1995 | Scott et al. |
| 5,415,664 A | | 5/1995 | Pinchuk |
| 5,419,760 A | | 5/1995 | Narciso |
| 5,545,208 A | | 8/1996 | Wolff et al. |
| 5,549,663 A | | 8/1996 | Cottone |
| 5,575,818 A | | 11/1996 | Pinchuk |
| 5,591,227 A | | 1/1997 | Dinh et al. |
| 5,609,629 A | | 3/1997 | Fearnot et al. |
| 5,624,411 A | | 4/1997 | Tuch |
| 5,628,788 A | | 5/1997 | Pinchuk |
| 5,632,772 A | | 5/1997 | Alcime et al. |
| 5,637,113 A | | 6/1997 | Tartaglia et al. |
| 5,639,278 A | | 6/1997 | Dereume et al. |
| 5,653,747 A | | 8/1997 | Dereume |
| 5,697,967 A | | 12/1997 | Dinh et al. |
| 5,700,269 A | | 12/1997 | Pinchuk et al. |
| 5,723,004 A | | 3/1998 | Dereume et al. |
| 5,725,567 A | | 3/1998 | Wolff et al. |
| 5,733,327 A | | 3/1998 | Igaki et al. |
| 5,741,333 A | | 4/1998 | Frid |
| 5,749,921 A | | 5/1998 | Lenker et al. |
| 5,755,722 A | | 5/1998 | Barry et al. |
| 5,755,774 A | | 5/1998 | Pinchuk |
| 5,766,710 A | | 6/1998 | Turnlund et al. |
| 5,797,887 A | | 8/1998 | Rosen et al. |
| 5,824,048 A | | 10/1998 | Tuch |
| 5,824,049 A | | 10/1998 | Ragheb et al. |
| 5,837,008 A | | 11/1998 | Berg et al. |
| 5,843,172 A | | 12/1998 | Yan |
| 5,849,037 A | | 12/1998 | Frid |
| 5,855,598 A | | 1/1999 | Pinchuk |
| 5,871,538 A | | 2/1999 | Dereume |
| 5,900,246 A | | 5/1999 | Lambert |
| 5,928,247 A | | 7/1999 | Barry et al. |
| 5,938,697 A | | 8/1999 | Killion et al. |
| 5,948,018 A | | 9/1999 | Dereume et al. |
| 5,968,070 A | | 10/1999 | Bley et al. |
| 5,968,091 A | | 10/1999 | Pinchuk et al. |
| 5,980,551 A | | 11/1999 | Summers et al. |
| 5,980,972 A | | 11/1999 | Ding |
| 6,001,125 A | | 12/1999 | Golds et al. |
| 6,004,346 A | | 12/1999 | Wolff et al. |
| 6,013,099 A | | 1/2000 | Dinh et al. |
| 6,017,362 A | | 1/2000 | Lau et al. |
| 6,019,789 A | | 2/2000 | Dinh et al. |
| 6,102,212 A | | 8/2000 | Strid |
| 6,102,939 A | | 8/2000 | Pinchuk |
| 6,106,913 A | | 8/2000 | Scardino et al. |
| 6,117,425 A | | 9/2000 | MacPhee et al. |
| 6,165,212 A | | 12/2000 | Dereume et al. |
| 6,252,129 B1 | | 6/2001 | Coffee |
| 6,265,333 B1 | | 7/2001 | Dzenis et al. |
| 6,270,793 B1 | | 8/2001 | Van Dyke et al. |
| 6,306,424 B1 | | 10/2001 | Vyakarnam et al. |
| 6,308,509 B1 | | 10/2001 | Scardino et al. |
| 6,309,413 B1 | | 10/2001 | Dereume et al. |
| 6,604,925 B1 | | 8/2003 | Dubson |
| 2001/0020652 A1 | | 9/2001 | Kadlubowski et al. |
| 2002/0002395 A1 | | 1/2002 | Berg et al. |

FOREIGN PATENT DOCUMENTS

| | | |
|---|---|---|
| EP | 0253539 | 1/1988 |
| EP | 0523960 | 1/1993 |
| GB | 2142870 | 1/1985 |
| WO | WO 01/54667 | 2/2001 |
| WO | WO 02/40242 | 5/2002 |

\* cited by examiner

METHOD AND APPARATUS FOR MANUFACTURING POLYMER FIBER SHELLS VIA ELECTROSPINNING

RELATED PATENT APPLICATION

This application is a National Phase Application of PCT/LL01/01168 International Filing Date 17 Dec. 2001, which claims priority from U.S. patent application No. 09,982,017 filed 19 Oct. 2001, which claims priority from U.S. Provisional patent application Nos. 60,276,956 filed 20 Mar. 2001 and 60,256,323 filed 19 Dec. 2000.

FIELD AND BACKGROUND OF THE INVENTION

The present invention relates to a method and apparatus for manufacturing polymer fiber shells via electrospinning.

Polymer fiber shells such as tubular shaped products, are used in the medical industry for various utilities including esophageal grafts, vascular grafts, stent coats and like.

Numerous methods for manufacturing polymer fiber shells suitable for medical applications are known in the art, including, for example, various injection molding methods, mandrel assisted extrusion or formation and various weaving techniques.

Production of polymer fiber shells suitable for use as vascular grafts is particularly difficult, since such grafts must withstand high and pulsatile blood pressures while, at the same time, be elastic and biocompatible.

Vascular grafts known in the art typically have a microporous structure that in general allows tissue growth and cell endothelization, thus contributing to long term engraftment and patency of the graft.

In vascular grafts, tissue ingrowth and cell endothelization is typically enhanced with increased in grafts exhibiting increased porosity. However, increasing the porosity of vascular grafts leads to a considerable reduction of the mechanical and tensile strength of the graft, and as a consequence to a reduction in the functionality thereof.

Electrospinning has been used for generating various products for medical applications, e.g., wound dressings, prosthetic devices, and vascular grafts as well as for industrial use, e.g., electrolytic cell diaphragms, battery separators, and fuel cell components. It has already been proposed to produce by electrospinning products having the appearance of shells. For example, U.S. Pat. No. 4,323,525 discloses a method of preparing a tubular product by electrostatically spinning a fiber forming material and collecting the resulting spun fibers on a rotating mandrel. U.S. Pat. No. 4,552,707 discloses a varying rotation rate mandrel which controls the "anisotropy extent" of fiber orientation of the final product. Additional examples of tubular shaped products and a like are disclosed, e.g., in U.S. Pat. Nos. 4,043,331, 4,127,706, 4,143,196, 4,223,101, 4,230,650 and 4,345,414.

The process of electrospinning creates a fine stream or jet of liquid that upon proper evaporation yields a non-woven fiber structure. The fine stream of liquid is produced by pulling a small amount of a liquefied polymer (either polymer dissolved in solvent (polymer solution) or melted polymer) through space using electrical forces. The produced fibers are then collected on a suitably located precipitation device, such as a mandrel to form tubular structures. In the case of a melted polymer which is normally solid at room temperature, the hardening procedure may be mere cooling, however other procedures such as chemical hardening or evaporation of solvent may also be employed.

In electrospinning, an electric field with high filed lines density (i.e., having large magnitude per unit volume) may results in a corona discharge near the precipitation device, and consequently prevent fibers from being collected by the precipitation device. The filed lines density of an electric field is determined inter alia by the geometry of the precipitation device; in particular, sharp edges on the precipitation device increase the effect of corona discharge.

In addition, due to the effect of electric dipole rotation along the electric field maximal strength vector in the vicinity of the mandrel, products with at least a section with a small radius of curvature are coated coaxially by the fibers. Such structural fiber formation considerably reduces the radial tensile strength of a spun product, which, in the case of vascular grafts, is necessary for withstanding pressures generated by blood flow.

Various electrospinning based manufacturing methods for generating vascular grafts are known in the prior art, see, for example, U.S. Pat. Nos. 4,044,404, 4,323,525, 4,738,740, 4,743,252, and 5,575,818. However, such methods suffer from the above inherent limitations which limit the use thereof when generating intricate profile fiber shells.

Hence, although electrospinning can be efficiently used for generating large diameter shells, the nature of the electrospinning process prevents efficient generation of products having an intricate profile and/or small diameter, such as vascular grafts. In particular, since porosity and radial strength are conflicting, prior art electrospinning methods cannot be effectively used for manufacturing vascular grafts having both characteristics.

There is thus a widely recognized need for, and it would be highly advantageous to have, a method and apparatus for manufacturing polymer fiber shells via electrospinning devoid of the above limitations.

SUMMARY OF THE INVENTION

According to one aspect of the present invention there is provided an apparatus for manufacturing polymer fiber shells from liquefied polymer, the apparatus comprising: (a) a precipitation electrode being for generating the polymer fiber shell thereupon; (b) a dispenser, being at a first potential relative to the precipitation electrode so as to generate an electric field between the precipitation electrode and the dispenser, the dispenser being for: (i) charging the liquefied polymer thereby providing a charged liquefied polymer; and (ii) dispensing the charged liquefied polymer in a direction of the precipitation electrode; and (c) a subsidiary electrode being at a second potential relative to the precipitation electrode, the subsidiary electrode being for modifying the electric field between the precipitation electrode and the dispenser.

According to another aspect of the present invention there is provided a method for forming a liquefied polymer into a non-woven polymer fiber shells, the method comprising: (a) charging the liquefied polymer thereby producing a charged liquefied polymer; (b) subjecting the charged liquefied polymer to a first electric field; (c) dispensing the charged liquefied polymer within the first electric field in a direction of a precipitation electrode, the precipitation electrode being designed and configured for generating the polymer fiber shell; (d) providing a second electric field being for modifying the first electric field; and (e) using the precipitation electrode to collect the charged liquefied polymer thereupon, thereby forming the non-woven polymer fiber shell.

According to further features in preferred embodiments of the invention described below, the first electric field is defined between the precipitation electrode and a dispensing electrode being at a first potential relative to the precipitation electrode.

According to still further features in the described preferred embodiments step (c) is effected by dispensing the charged liquefied polymer from the dispensing electrode.

According to still further features in the described preferred embodiments the second electric field is defined by a subsidiary electrode being at a second potential relative to the precipitation electrode.

According to still further features in the described preferred embodiments the subsidiary electrode serves for reducing non-uniformities in the first electric field According to still further features in the described preferred embodiments the subsidiary electrode serves for controlling fiber orientation of the polymer fiber shell generated upon the precipitation electrode.

According to still further features in the described preferred embodiments the subsidiary electrode serves to minimize a volume charge generated between the dispenser and the precipitation electrode.

According to still further features in the described preferred embodiments the method further comprising moving the subsidiary electrode along the precipitation electrode during step (e).

According to still further features in the described preferred embodiments the method further comprising moving the dispensing electrode along the precipitation electrode during step (c).

According to still further features in the described preferred embodiments the method further comprising synchronizing the motion of the dispensing electrode and the subsidiary electrode along the precipitation electrode.

According to still further features in the described preferred embodiments the dispenser comprises a mechanism for forming a jet of the charged liquefied polymer.

According to still further features in the described preferred embodiments the apparatus further comprising a bath for holding the liquefied polymer.

According to still further features in the described preferred embodiments the mechanism for forming a jet of the charged liquefied polymer includes a dispensing electrode.

According to still further features in the described preferred embodiments the dispenser is operative to move along a length of the precipitation electrode.

According to still further features in the described preferred embodiments the precipitation electrode includes at least one rotating mandrel.

According to still further features in the described preferred embodiments the rotating mandrel is a cylindrical mandrel.

According to still further features in the described preferred embodiments the rotating mandrel is an intricate-profile mandrel.

According to still further features in the described preferred embodiments the intricate-profile mandrel includes sharp structural elements.

According to still further features in the described preferred embodiments the cylindrical mandrel is of a diameter selected from a range of 0.1 to 20 millimeters.

According to still further features in the described preferred embodiments the precipitation electrode includes at least one structural element selected from the group consisting of a protrusion, an orifice, a groove, and a grind.

According to still further features in the described preferred embodiments the subsidiary electrode is of a shape selected from the group consisting of a plane, a cylinder, a torus and a wire.

According to still further features in the described preferred embodiments the subsidiary electrode is operative to move along a length of the precipitation electrode.

According to still further features in the described preferred embodiments the subsidiary electrode is tilted at angle with respect to a longitudinal axis of the precipitation electrode, the angle is ranging between 45 and 90 degrees.

According to still further features in the described preferred embodiments the subsidiary electrode is positioned at a distance of 5–70 millimeters from the precipitation electrode.

According to still further features in the described preferred embodiments the subsidiary electrode is positioned at a distance $\delta$ from the precipitation electrode, $\delta$ being equal to $12\beta R(1-V_2/V_1)$, where $\beta$ is a constant ranging between about 0.7 and about 0.9, R is the curvature-radius of the polymer fiber shell formed on the precipitation electrode, $V_1$ is the first potential and $V_2$ is the second potential.

According to yet another aspect of the present invention there is provided an apparatus for manufacturing a polymer fiber shells from liquefied polymer, the apparatus comprising: (a) a dispenser, for: (i) charging the liquefied polymer thereby providing a charged liquefied polymer; and (ii) dispensing the charged liquefied polymer; and (b) a precipitation electrode being at a potential relative to the dispenser thereby generating an electric field between the precipitation electrode and the dispenser, the precipitation electrode being for collecting the charged liquefied polymer drawn by the electric field, to thereby form the polymer fiber shell thereupon, wherein the precipitation electrode is designed so as to reduce non-uniformities in the electric field.

According to still further features in the described preferred embodiments the precipitation electrode is formed from a combination of electroconductive and non-electroconductive materials.

According to still further features in the described preferred embodiments a surface of the precipitation electrode is formed by a predetermined pattern of the electroconductive and non-electroconductive materials.

According to still further features in the described preferred embodiments the precipitation electrode is formed from at least two layers.

According to still further features in the described preferred embodiments the at least two layers include an electroconductive layer and a partial electroconductive layer.

According to still further features in the described preferred embodiments the partial electroconductive layer is partial electroconductive layer is formed from a combination of an electroconductive material and at least one dielectric material.

According to still further features in the described preferred embodiments the dielectric material is selected from a group consisting of polyamide and polyacrylonitrile and polytetrafluoroethylene.

According to still further features in the described preferred embodiments the dielectric material is Titanium Nitride.

According to still further features in the described preferred embodiments the partial electroconductive layer, is selected of a thickness ranging between 0.1 to 90 microns.

The present invention successfully addresses the shortcomings of the presently known configurations by providing an electrospinning apparatus and method capable of fabricating a non-woven polymer fiber shell which can be used in vascular grafts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method and an apparatus for manufacturing a polymer fiber shell using electrospinning. Specifically, the present invention can be used to manufacture intricate-profile products and vascular grafts of small to large diameter via electrospinning.

Figure 1:
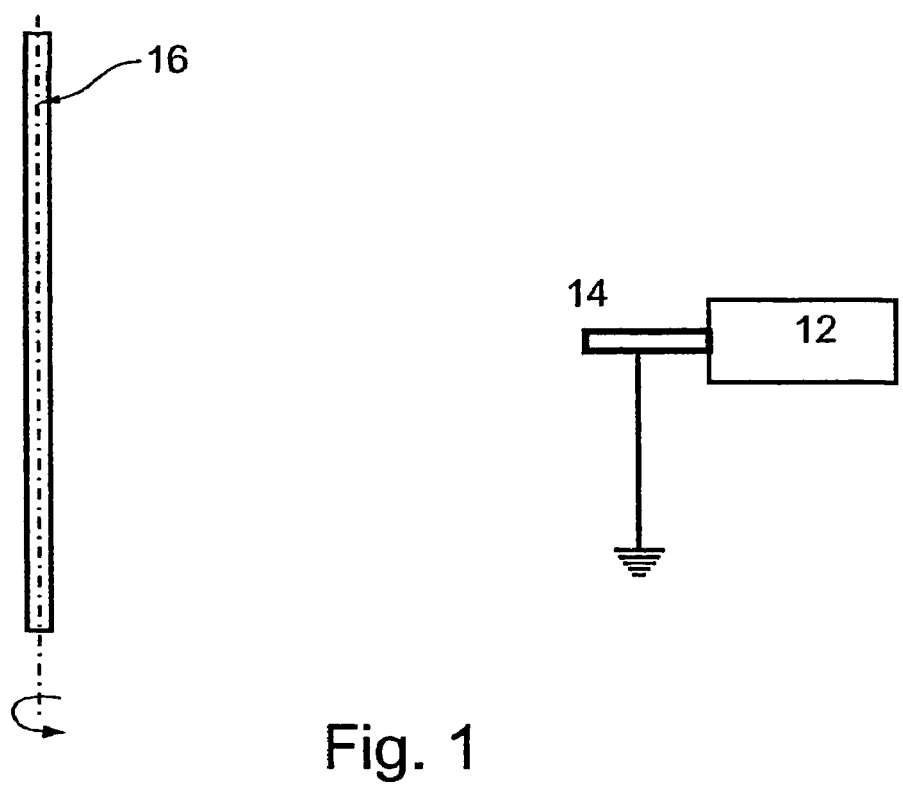
FIG. 1 is a schematic illustration of a prior art electrospinning apparatus.

For purposes of better understanding the present invention, as illustrated in FIGS. 2–10 of the drawings, reference is first made to the construction and operation of a conventional (i.e., prior art) electrospinning apparatus as illustrated in FIG. 1.

FIG. 1 illustrates an apparatus for manufacturing a tubular structure using a conventional electrospinning apparatus, which is referred to herein as apparatus 10.

Apparatus 10 includes a dispenser 12 which can be, for example, a bath provided with capillary apertures 14. Dispenser 12 serves for storing the polymer to be spun in a liquid form. Dispenser 12 is positioned at a predetermined distance from a precipitation electrode 16.

Precipitation electrode 16 serves for generating the tubular structure thereupon. Precipitation electrode 16 is typically manufactured in the form of a mandrel or any other cylindrical structure. Precipitation electrode 16 is rotated by a mechanism such that a tubular structure is formed when coated with the polymer.

Dispenser 12 is typically grounded, while precipitation electrode 16 is connected to a source of high voltage preferably of negative polarity, thus forming an electric field between dispenser 12 and precipitation electrode 16. Alternatively, precipitation electrode 16 can be grounded while dispenser 12 is connected to a source of high voltage, preferably with positive polarity.

To generate a tubular structure, a liquefied polymer (e.g., melted polymer or dissolved polymer) is extruded, for example under the action of hydrostatic pressure, through capillary apertures 14 of dispenser 12. As soon as meniscus forms from the extruded liquefied polymer, a process of solvent evaporation or cooling starts which is accompanied by the creation of capsules with a semi-rigid envelope or crust. An electric field, occasionally accompanied a by unipolar corona discharge in the area of dispenser 12, is generated by the potential difference between dispenser 12 and precipitation electrode 16. Because the liquefied polymer possesses a certain degree of electrical conductivity, the above-described capsules become charged. Electric forces of repulsion within the capsules lead to a drastic increase in hydrostatic pressure. The semi-rigid envelopes are stretched, and a number of point micro-ruptures are formed on the surface of each envelope leading to spraying of ultra-thin jets of liquefied polymer from dispenser 12.

The charges tend to distribute along the jets, thus preventing existence of any non-zero component of electric field inside the jet. Thus, a conduction current flows along the jets, which results in the accumulation of (different sign) free charges on the liquefied polymer surface.

Under the effect of a Coulomb force, the jets depart from the dispenser 12 and travel towards the opposite polarity electrode, i.e., precipitation electrode 16. Moving with high velocity in the inter-electrode space, the jet cools or solvent therein evaporates, thus forming fibers which are collected on the surface of precipitation electrode 16. Since electrode 16 is rotating the charged fibers form a tubular shape.

When using mandrels being at least partially with small radius of curvature, the orientation of the electric field maximal strength vector is such that precipitation electrode 16 is coated coaxially by the fibers. Thus, small diameter products, have limited radial strength when manufactured via existing electrospinning methods, as described above.

When using mandrels with sharp edges and/or variously shaped and sized recesses, the electric field magnitude in the vicinity of precipitation electrode 16 may exceed the air electric strength (about 30 kV/cm), and a corona discharge may develop in the area of precipitation electrode 16. The effect of corona discharge decreases the coating efficiency of the process as described hereinbelow, and may even resultant in a total inability of fibers to be collected upon precipitation electrode 16.

Corona discharge initiation is accompanied by the generation of a considerable amount of air ions having opposite charge sign with respect to the charged fibers. Since an electric force is directed with respect to the polarity of charges on which it acts, theses ions start to move at the opposite direction to fibers motion i.e., from precipitation electrode 16 towards dispenser 12. Consequently, a portion of these ions generate a volume charge (ion cloud), non-uniformly distributed in the inter-electrode space, thereby causing electric field lines to partially close on the volume charge rather than on precipitation electrode 16. Moreover, the existence of an opposite volume charge in the inter-electrode space, decreases the electric force on the fibers, thus resulting in a large amount of fibers accumulating in the inter-electrode space and gradually settling under gravity force. It will be appreciated that such an effect leads to a low-efficiency process of fiber coating.

Using an infinite-length/radius cylinder as a precipitation electrode 16 diminishes the effect described above. However, this effect is severe and limiting when small radii or complicated mandrels are employed for fabricating small radius or intricate-profile structures.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

While reducing the present invention to practice, it was uncovered that the use of a third electrode within an electrospinning apparatus enables to control the electric field generated between the dispenser and precipitation electrode. Specifically, a third electrode may either substantially decreases non-uniformities in the electric field or provides for controlled fiber orientation upon deposition.

Thus, according to the present invention there is provided an apparatus for manufacturing a polymer fiber shell from a liquefied polymer, which apparatus is referred to herein as apparatus 20.

Figure 2:
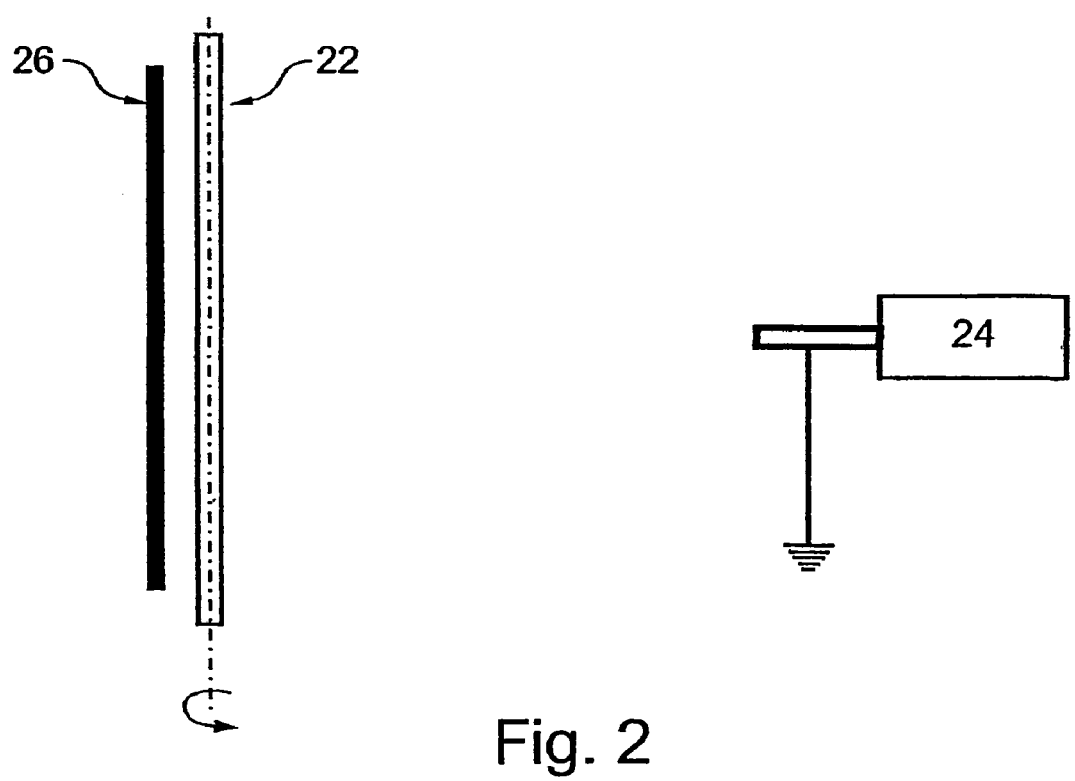
FIG. 2 is a schematic illustration of an electrospinning apparatus which includes a subsidiary electrode according to the teachings of the present invention.
Figure 3:
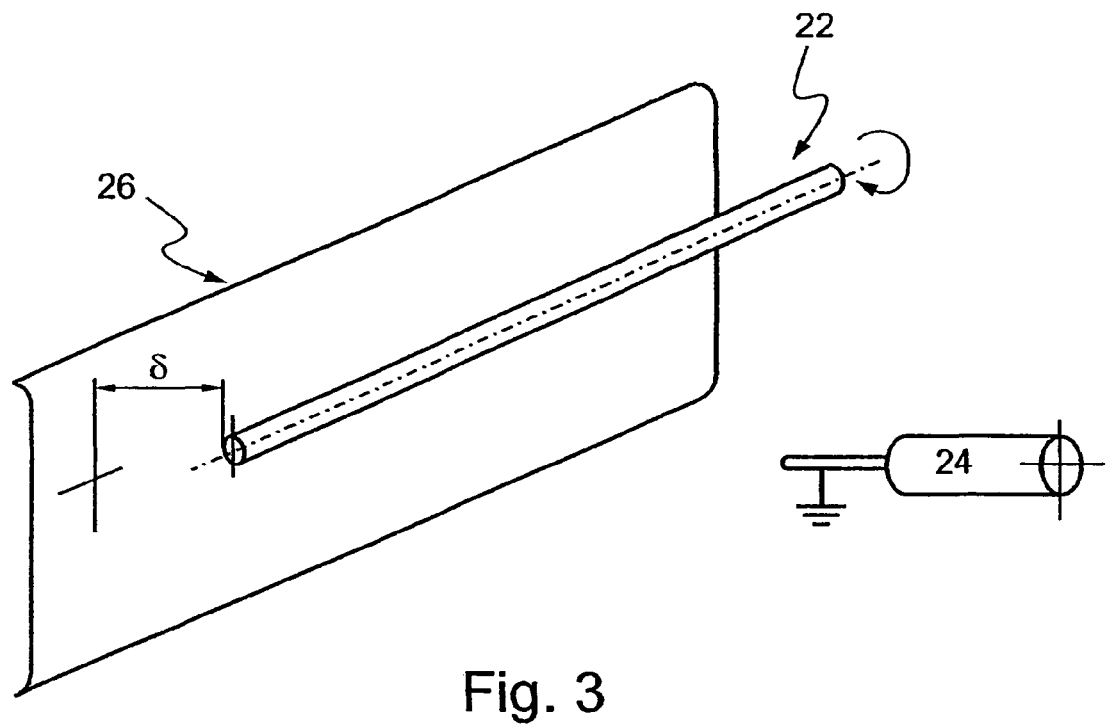
FIG. 3 is a schematic illustration of an electrospinning apparatus which includes a planar subsidiary electrode according to the teachings of the present invention.
Figure 4:
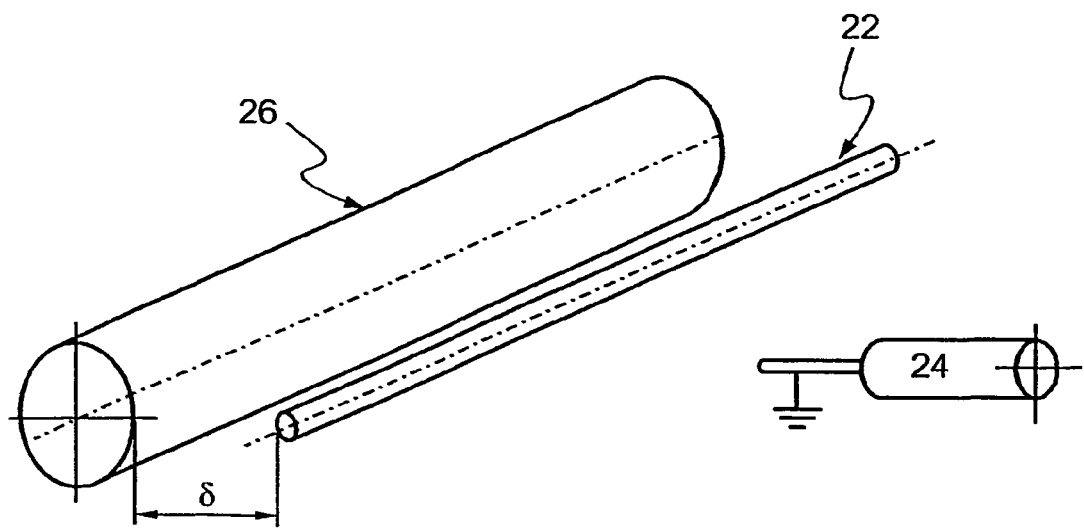
FIG. 4 is a schematic illustration of an electrospinning apparatus which includes a cylindrical subsidiary electrode according to the teachings of the present invention.

As shown in FIG. 2, apparatus 20 includes a precipitation electrode 22 which serves for generating the polymer fiber shell thereupon. Precipitation electrode 22 can be, for example, a mandrel of uniform or varying radius, which may include some structural elements such as, but not limited to, protrusions, orifices and grooves. The surface of precipitation electrode 22 may also contain grinds. The diameter of the mandrel may vary from about 0.1 millimeter up to about 20 millimeters depending on the diameter of the polymer fiber shell to be spun thereupon.

Apparatus 20 further includes a dispenser 24, which is at a first potential relative to precipitation electrode 22. Such a potential can be generated by grounding dispenser 24, and connecting a source of high voltage with negative polarity to precipitation electrode 22.

Alternatively, precipitation electrode 22 can be grounded while dispenser 24 is connected to a source of high voltage with positive polarity. In any case, an absolute value for the potential difference between dispenser 24 and precipitation electrode 22 may range between about 10 kV and about 100 kV.

The potential difference between dispenser 24 and precipitation electrode 22 ensures that an electric field is maintained therebetween, which electric field is important for the electrospinning process as described hereinabove.

Dispenser 24 serves for charging the liquefied polymer, thereby providing a charged liquefied polymer and dispensing the charged liquefied polymer in a direction of precipitation electrode 22. Dispenser 24 may also include a mechanism for moving it along a longitudinal axis of precipitation electrode 22, thus enabling dispensing of the charged liquefied polymer at various points along the longitudinal axis of precipitation electrode 22.

The charged liquefied polymer may be, for example polyurethane, polyester, polyolefin, polymethyl methacrylate, polyvinyl aromatic, polyvinyl ester, polyamide, polyimide, polyether, polycarbonate, polyacrilonitrile, polyvinyl pyrrolidone, polyethylene oxide, poly (L-lactic acid), poly (lactide-CD-glycoside), polycaprolactone, polyphosphate ester, poly (glycolic acid), poly (DL-lactic acid), and some copolymers. Biolmolecules such as DNA, silk, chitozan and cellulose may also be used. Improved charging of the polymer may also be required. Improved charging is effected according to the present invention by mixing the liquefied polymer with a charge control agent (e.g., a dipolar additive) to form, for example, a polymer-dipolar additive complex which apparently better interacts with ionized air molecules formed under the influence of the electric field. It is assumed, in a non-limiting fashion, that the extra-charge attributed to the newly formed fibers is responsible for their more homogenous precipitation on the precipitation electrode, wherein a fiber is better attracted to a local maximum, which is a local position most under represented by older precipitated fibers, which keep their charge for 5–10 minutes. The charge control agent is typically added in the grams equivalent per liter range, say, in the range of from about 0.001 N to about 0.1 N, depending on the respective molecular weights of the polymer and the charge control agent used.

U.S. Pat. Nos. 5,726,107; 5,554,722; and 5,558,809 teach the use of charge control agents in combination with polycondensation processes in the production of electret fibers, which are fibers characterized in a permanent electric charge, using melt spinning and other processes devoid of the use of an precipitation electrode. A charge control agent is added in such a way that it is incorporated into the melted or partially melted fibers and remains incorporated therein to provide the fibers with electrostatic charge which is not dissipating for prolonged time periods, say months.

In a preferred embodiment of the present invention, the charge control agent transiently binds to the outer surface of the fibers and therefore the charge dissipates shortly thereafter (within minutes). This is because polycondensation is not exercised at all such the chemical intereaction between the agent and the polymer is absent, and further due to the low concentration of charge control agent employed. The resulting shell is therefore substantially charge free.

Suitable charge control agents include, but are not limited to, mono- and poly-cyclic radicals that can bind to the polymer molecule via, for example, —C=C—, =C—SH— or —CO—NH— groups, including biscationic amides, phenol and uryl sulfide derivatives, metal complex compounds, triphenylmethanes, dimethylmidazole and ethoxytrimethylsians.

Typically, the charged liquefied polymer is dispensed as a liquid jet, moving at high velocity under electrical forces caused by the electric field. Thus, dispenser 24 typically includes a bath for holding the liquefied polymer and a mechanism for forming a jet, which mechanism may be, for example, a dispensing electrode.

Apparatus 20 further includes at least one subsidiary electrode 26 which is at a second potential relative to precipitation electrode 22. Subsidiary electrode 26 serves for controlling the direction and magnitude of the electric field between precipitation electrode 22 and dispenser 24 and as such, subsidiary electrode 26 can be used to control the orientation of polymer fibers deposited on precipitation electrode 22. In some embodiments, subsidiary electrode 26 serves as a supplementary screening electrode. Broadly stated, use of screening results in decreasing the coating precipitation factor, which is particularly important upon mandrels having at least a section of small radii of curvature.

The size, shape, position and number of subsidiary electrode 26 is selected so as to maximize the coating precipitation factor, while minimizing the effect of corona discharge in the area of precipitation electrode 22 and/or so as to provide for controlled fiber orientation upon deposition.

According to one preferred embodiment of the present invention, subsidiary electrode 26 is positioned 5–70 mm away from precipitation electrode 22.

Preferably, such a distance is selected according to the following:

$$\delta = 12\beta R(1 - V_2/V_1) \qquad \text{(Eq. 1)}$$

where $\beta$ is a dimensionless constant named a fiber-charge accounting factor, which ranges between about 0.7 and about 0.9, R is the curvature-radius of precipitation electrode 22, $V_1$ is the potential difference between dispenser 24 and precipitation electrode 22 and $V_2$ is the potential difference between subsidiary electrode 26 and precipitation electrode 22.

Subsidiary electrode 26 may include a mechanism for moving it along a longitudinal axis of precipitation electrode 22. Such a mechanism may be in use when enhanced control over fiber orientation is required.

It will be appreciated that in an apparatus in which both dispenser 24 and subsidiary electrode 26 are capable of such longitudinal motion, such motion may be either independent or synchronized.

Subsidiary electrode 26 may also be tilted through an angle of 45–90 degrees with respect to the longitudinal axis of precipitation electrode 22. Such tilting may be used to provide for controlled fiber orientation upon deposition, hence to control the radial strength of the manufactured shell; specifically, large angles result in higher radial strength.

In addition to positioning, the shape and size of electrode 26 may also determine the quality of the shell formed by apparatus 20. Thus, electrode 26 may be fabricated in a variety of shapes each serving a specific purpose. Electrode shapes which can be used with apparatus 20 of the present invention include, but are not limited to, a plane, a cylinder, a torus a rod, a knife, an arc or a ring.

Figure 8:
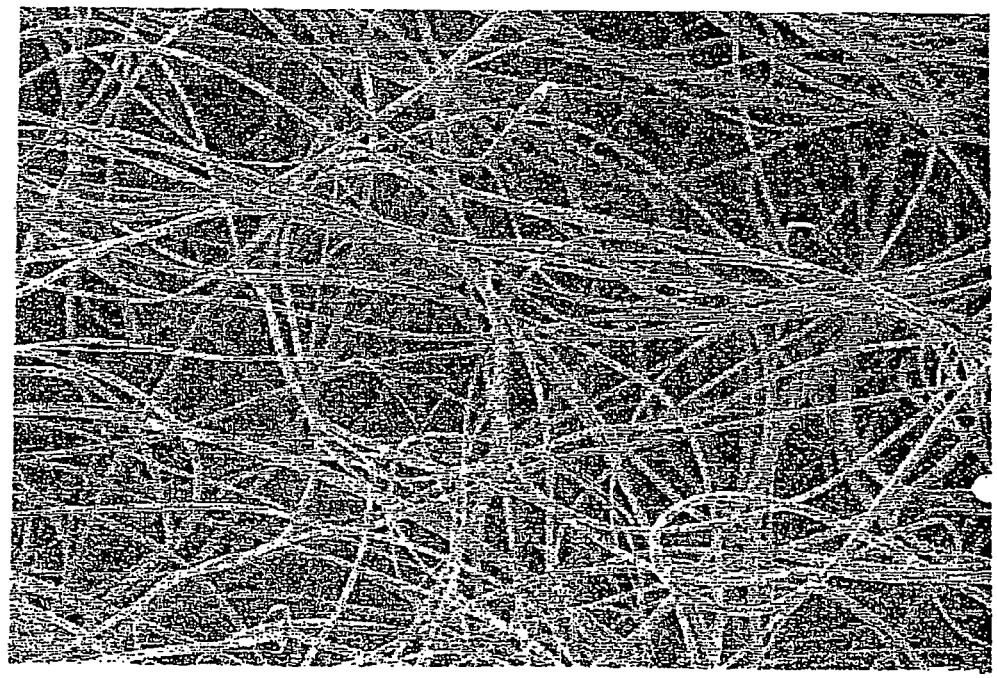
FIG. 8 is an electron microscope image of material spun using an apparatus which incorporates a flat subsidiary electrode, positioned 20 millimeters from the mandrel, according to the teachings of the present invention.
Figure 9:
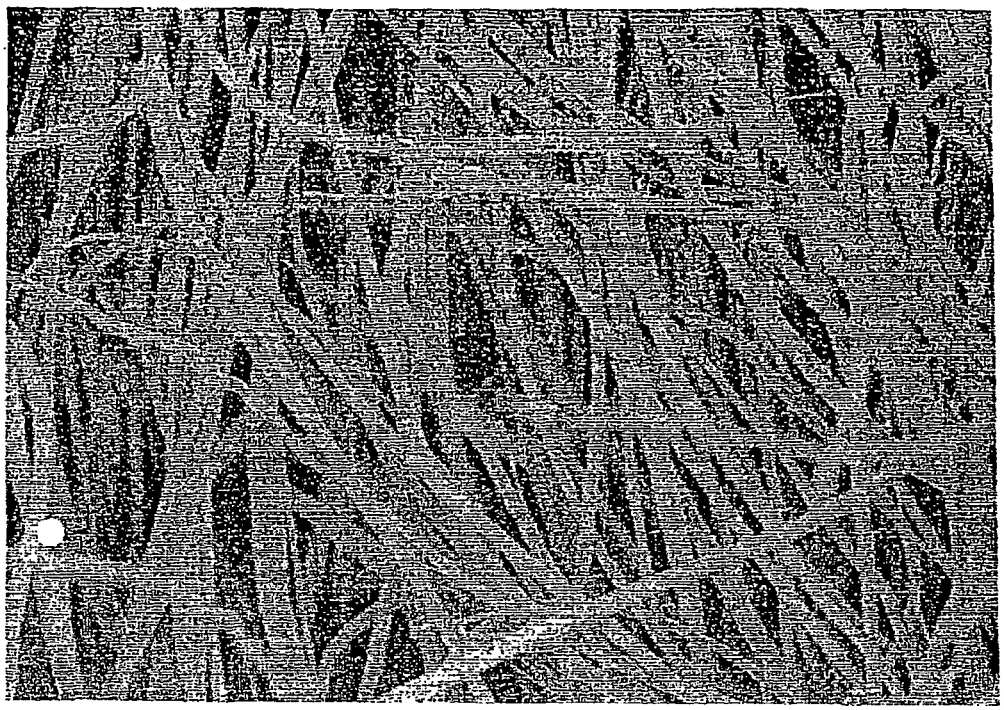
FIG. 9 is an electron microscope image of material spun using an apparatus which incorporates a flat subsidiary electrode, positioned 9 millimeters from the mandrel, according to the teachings of the present invention.

An apparatus 20 which includes a subsidiary electrode 26 of a cylindrical (FIG. 4) or a flat shape (FIG. 3) enables manufacturing intricate-profile products being at least partially with small radius of curvature, which radius may range between 0.025 millimeters and 5 millimeters. As can be seen in FIGS. 8–9 (further described in the Examples section), the coating of such structures is characterized by random-oriented (FIG. 8) or even polar-oriented (FIG. 9) fibers, as opposed to an axial coating which is typical for small curvature products manufactured via existing electrospinning methods as demonstrated in FIG. 7 (further described in the Examples section).

Preferably, when a surface of large curvature is used as subsidiary electrode 26, as is the case above, the distance between subsidiary electrode 26 and precipitation electrode 22 can be determined as $\delta/x$ where x is a factor ranging between 1.8 and 2, and where $\delta$ is as defined by Equation 1 above.

Thus, positioning and/or shape of electrode 26 determines fiber orientation in the polymer fiber shell formed.

The ability to control fiber orientation is important when fabricating vascular grafts in which a high radial strength and elasticity is important. It will be appreciated that a polar oriented structure can generally be obtained also by wet spinning methods, however in wet spinning methods the fibers are thicker than those used by electrospinning by at least an order of magnitude.

Control over fiber orientation is also advantageous when fabricating composite polymer fiber shells which are manufactured by sequential deposition of several different fiber materials.

Figure 5:
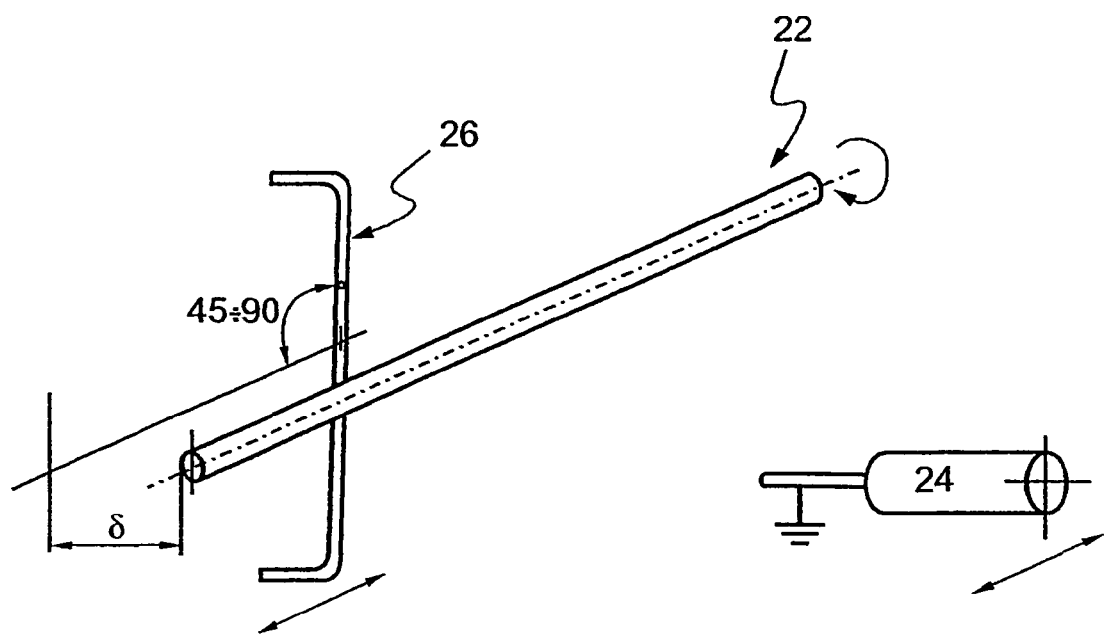
FIG. 5 is a schematic illustration of an electrospinning apparatus which includes a linear subsidiary electrode according to the teachings of the present invention.

Reference is now made to FIG. 5, which illustrates an apparatus 20 which utilizes a linear (e.g., a rod, a knife, an arc or a ring) subsidiary electrode 26.

Figure 10:
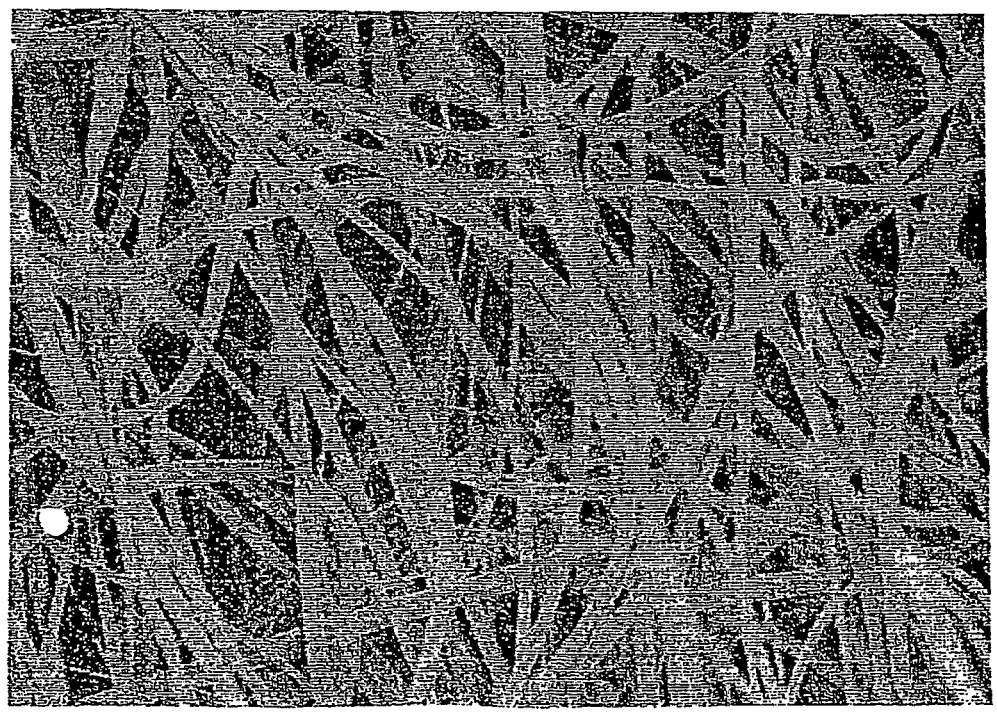
FIG. 10 is an electron microscope image of polar-oriented material spun using an apparatus which incorporates a linear subsidiary electrode according to the teachings of the present invention.

The effect of subsidiary electrode 26 of linear shape is based on the distortion it introduces to the electric field in an area adjacent to precipitation electrode 22. For maximum effect the diameter of subsidiary electrode 26 must be considerably smaller than that of precipitation electrode 22, yet large enough to avoid generation of a significant corona discharge. Fiber coating generated by apparatus 20 utilizing a linear subsidiary electrode 26 is illustrated by FIG. 10 which is further described in the Examples section hereinunder.

Thus, the present invention provides an electrospinning apparatus in which the electric field is under substantial control, thereby providing either random or predetermined fibers orientation.

Although the use of at least one subsidiary electrode is presently preferred, field non-uniformities can also be at least partially overcome by providing a composite precipitation electrode.

Figure 6:
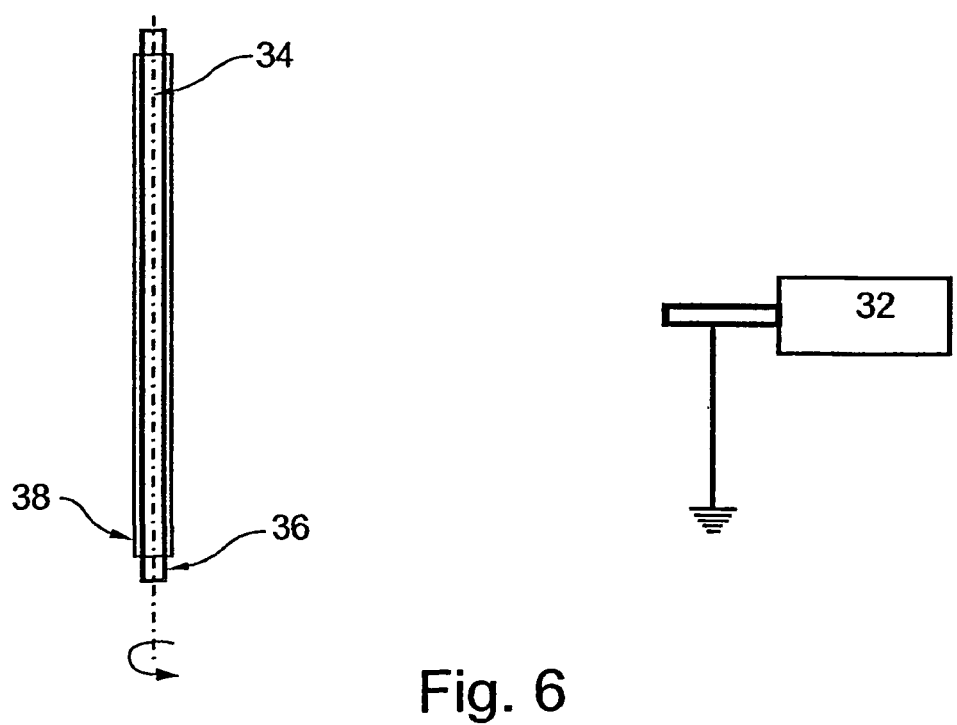
FIG. 6 is a schematic illustration of an electrospinning apparatus which includes a composite subsidiary electrode according to the teachings of the present invention.

As illustrated in FIG. 6, precipitation electrode 34 of apparatus 30 having a dispenser 32 can be designed and configured so as to reduce non-uniformities in the electric field.

To overcome field non-uniformities, precipitation electrode 34 is fabricated from at least two layers of materials, an inner layer 36 made of electroconductive material and an outer layer 38 made of a material having high dielectric properties. Such a fabrication design results in a considerable increase of corona discharge threshold thus considerably reducing corona discharge from precipitation electrode 34.

Materials suitable for use with outer layer 38 of precipitation electrode 34, can be ceramic materials e.g., Titanium Nitride, Aluminum Oxide and the like, or polymer materials e.g., polyamide, polyacrylonitrile, polytetrafluoroethylene and the like. The thickness of outer layer 38 depends on the dielectric properties of the material from which it is made and can vary from less than one micron, in the case of, for example, a Titanium Nitride layer, or tens of microns, in the case of, for example, polytetrafluoroethylene, polyamide or polyacrylonitrile layer. In addition to diminishing corona discharge this precipitation electrode configuration enables easier separation of formed structures therefrom. Thus, according to this configuration outer layer 38 of precipitation electrode 34 can also be configured for facilitating the removal of the final product from the mandrel.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Electrospinning Material

A polycarbonate resin grade Caliper 2071 was purchased from Daw Chemical Co. This Polymer is characterized as having good fiber forming abilities and is convenient for electrospinning. Chloroform was used as solvent in all of the examples described hereinbelow.

Example 1

Axial Covering Using Conventional Electrospinning Method

Figure 7:
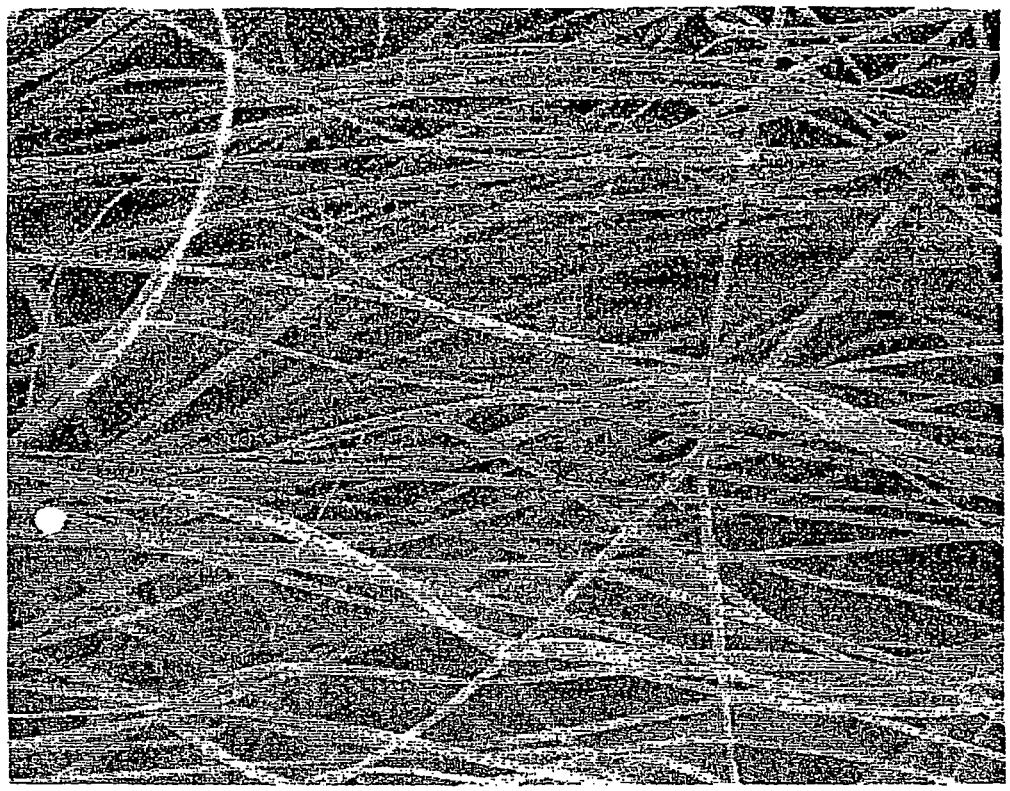
FIG. 7 is an electron microscope image of material spun using conventional electrospinning techniques.

Reference is now made to FIG. 7, which is an example of non-randomized covering of thin mandrels via conventional electrospinning. A 3-mm cylindrical mandrel was covered by polycarbonate fiber using prior art electrospinning approaches. FIG. 7 is an electron microscope image of the final product, in which axial fiber orientation is well evident. Due to non-uniformities in the electric field, the fibers, while still in motion in the inter-electrode space, are oriented in conformity with the field configuration, and the obtained tubular structure exhibits axial orientation of fibers, and as such is characterized by axial, as opposed to radial strength.

Example 2

Random Covering Using Flat Subsidiary Electrode

An apparatus constructed and operative in accordance with the teachings of the present invention incorporating a flat subsidiary electrode positioned 20 millimeters from the mandrel and having the same potential as the mandrel was used to spin a polycarbonate tubular structure of a 3 mm radius. As is evident from FIG. 8, the presence of a subsidiary electrode randomizes fibers orientation.

Example 3

Polar-Oriented Covering Using Flat Subsidiary Electrode

An apparatus constructed and operative in accordance with the teachings of the present invention incorporating a flat subsidiary electrode positioned 9 millimeters from the mandrel and being at a potential difference of 5 kV from the mandrel was used to spin a polycarbonate tubular structure of a 3 mm radius.

As illustrated by FIG. 9, reduction of equalizing electrode-mandrel distance results in polar-oriented covering. Thus, by keeping subsidiary electrode and mandrel within a relatively small distance, while providing a non-zero potential difference therebetween, leads to slow or no fiber charge dissipation and, as a result, the inter-electrode space becomes populated with fiber which are held statically in a stretched position, oriented perpendicular to mandrel symmetry axis. Once stretched, the fibers are gradually coiled around the rotating mandrel, generating a polar-oriented structure.

Example 4

Predefined Oriented Covering Using Linear Subsidiary Electrode

FIG. 10 illustrates result obtained from an apparatus configuration which may be employed in order to obtain a predefined oriented structural fiber covering.

An apparatus which includes an elliptical subsidiary electrode and a dispenser both moving along the longitudinal axis of the mandrel in a reciprocating synchronous movement was used to coat a 3-mm cylindrical mandrel with polycarbonate fiber. The subsidiary electrode had a large diameter of 120 mm, a small diameter of 117.6 mm and a thickness of 1.2 mm. The subsidiary electrode was positioned 15 mm from the mandrel, at an 80° tilt with respect to the mandrel symmetry axis.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for manufacturing polymer fiber shell from liquefied polymer, the apparatus comprising:
   (a) a precipitation electrode being for generating the polymer fiber shell thereupon;
   (b) a dispenser, being at a first potential relative to said precipitation electrode so as to generate an electric field between said precipitation electrode and said dispenser, said dispenser being for:
      (i) charging the liquefied polymer thereby providing a charged liquefied polymer; and
      (ii) dispensing said charged liquefied polymer in a direction of said precipitation electrode; and
   (c) a subsidiary electrode being at a second potential relative to said precipitation electrode, said subsidiary electrode being for reducing non-uniformities in said electric field between said precipitation electrode and said dispenser.

2. The apparatus of claim 1, wherein said subsidiary electrode serves for controlling fiber orientation of said polymer fiber shell generated upon said precipitation electrode.

3. The apparatus according to claim 1, further comprising a bath for holding the liquefied polymer.

4. The apparatus according to claim 1, wherein said dispenser is operative to move along a longitudinal axis of said precipitation electrode.

5. The apparatus according to claim 1, wherein said precipitation electrode includes at least one rotating mandrel.

6. The apparatus according to claim 5, wherein said rotating mandrel is a cylindrical mandrel.

7. The apparatus according to claim 5, wherein said rotating mandrel is an intricate-profile mandrel.

8. The apparatus according to claim 7, wherein said intricate-profile mandrel includes sharp structural elements.

9. The apparatus according to claim 1, wherein said subsidiary electrode is of a shape selected from the group consisting of a plane, a cylinder, a torus and a wire.

10. The apparatus according to claim 1, wherein said subsidiary electrode is operative to move along a longitudinal axis of said precipitation electrode.

11. The apparatus according to claim 1, wherein said subsidiary electrode is tilted at angle with respect to a longitudinal axis of said precipitation electrode, said angle is ranging between 45 and 90 degrees.

12. A method for forming a liquefied polymer into a non-woven polymer fiber shell, the method comprising:
 (a) charging the liquefied polymer thereby producing a charged liquefied polymer;
 (b) subjecting said charged liquefied polymer to a first electric field;
 (c) dispensing said charged liquefied polymer within said first electric field in a direction of a precipitation electrode, said precipitation electrode being designed and configured for generating the polymer fiber shell thereupon;
 (d) providing a second electric field being for reducing non-uniformities in said first electric field; and
 (e) using said precipitation electrode to collect said charged liquefied polymer thereupon, thereby forming the non-woven polymer fiber shells.

13. The method according to claim 12, wherein said first electric field is defined between said precipitation electrode and a dispensing electrode being at a first potential relative to said precipitation electrode.

14. The method according to claim 12, further comprising moving said dispensing electrode along a longitudinal axis of said precipitation electrode during step (c).

15. The method according to claim 1, further comprising moving a subsidiary electrode along said precipitation electrode during step (e), said subsidiary electrode being at a second potential relative to said precipitation electrode so as to define said second electric field.

16. An apparatus for manufacturing a polymer fiber shell from liquefied polymer, the apparatus comprising:
 (a) a dispenser, for:
  (i) charging the liquefied polymer thereby providing a charged liquefied polymer; and
  (ii) dispensing said charged liquefied polymer; and
 (b) a precipitation electrode being at a potential relative to said dispenser thereby generating an electric field between said precipitation electrode and said dispenser, said precipitation electrode being for collecting said charged liquefied polymer drawn by said electric field, to thereby form the polymer fiber shell thereupon, wherein said precipitation electrode is formed from a combination of electroconductive and non-electroconductive materials so as to reduce non-uniformities in said electric field.

17. The apparatus of claim 1, wherein said subsidiary electrode serves to minimize a volume charge generated between said dispenser and said precipitation electrode.

18. The apparatus according to claim 1, wherein said dispenser and said subsidiary electrode are operative to move synchronically along a longitudinal axis of said precipitation electrode.

19. The apparatus according to claim 16, wherein a surface of said precipitation electrode is formed from a predetermined pattern of said electroconductive and non-electroconductive materials.

20. The apparatus according to claim 16, wherein said precipitation electrode is formed from at least two layers.

21. The apparatus according to claim 20, wherein said at least two layers include an electroconductive layer and a partial electroconductive layer.

22. The apparatus according to claim 21, wherein said partial electroconductive layer is formed from a combination of an electroconductive material and at least one dielectric material.

23. The apparatus according to claim 22, wherein said dielectric material is selected from a group consisting of polyamide, polytetrafluoroethylene and polyacrylonitrile.

24. The apparatus according to claim 22, wherein said dielectric material is Titanium Nitride.

25. The apparatus according to claim 21, wherein said partially electroconductive layer, is of a thickness selected from a range of 0.1 to 90 microns.

26. The apparatus according to claim 6, wherein said precipitation electrode is of a diameter selected from a range of 0.1 to 20 millimeters.

27. The apparatus according to claim 16, wherein said precipitation electrode includes at least one rotating mandrel.

28. The apparatus according to claim 27, wherein said rotating mandrel is a cylindrical mandrel.

* * * * *